US006547735B1

(12) United States Patent
Henderson

(10) Patent No.: US 6,547,735 B1
(45) Date of Patent: Apr. 15, 2003

(54) PARTIAL RAYLINE VOLUMETRIC SCANNING ULTRASONIC DIAGNOSTIC IMAGING SYSTEM

(75) Inventor: Derek Henderson, Mill Creek, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/008,957

(22) Filed: Dec. 5, 2001

(51) Int. Cl.[7] .................................................. A61B 8/00
(52) U.S. Cl. ........................................ 600/443; 128/916
(58) Field of Search .................................. 600/437, 439, 600/440–447, 450–471; 73/625, 626; 367/7, 11, 130, 138; 128/916

(56) References Cited

U.S. PATENT DOCUMENTS

| 4,310,907 A | | 1/1982 | Tachita et al. |
|---|---|---|---|
| 4,582,065 A | | 4/1986 | Adams |
| 5,159,931 A | | 11/1992 | Pini |
| 5,181,514 A | | 1/1993 | Solomon et al. |
| 5,301,168 A | | 4/1994 | Miller |
| 5,492,121 A | * | 2/1996 | Lu ............................ 600/459 |
| 5,617,863 A | * | 4/1997 | Roundhill et al. .......... 600/447 |
| 5,699,805 A | * | 12/1997 | Seward et al. .............. 600/459 |
| 5,795,297 A | * | 8/1998 | Daigle ........................ 600/447 |
| 5,797,846 A | | 8/1998 | Seyed-Bolorforosh et al. |
| 5,840,034 A | * | 11/1998 | Amemiya et al. .......... 600/444 |
| 5,846,200 A | | 12/1998 | Schwartz |
| 5,865,750 A | | 2/1999 | Hatfield et al. |
| 5,931,784 A | * | 8/1999 | Kajiwara et al. ........... 600/441 |
| 5,967,985 A | | 10/1999 | Hayakawa |

OTHER PUBLICATIONS

McCann et al., "Multidimensional Ultrasonic Imaging for Cardiology," pp. 1063–1073, Proceedings of the IEEE, vol. 76, No. 9, Sep. 1988.

* cited by examiner

Primary Examiner—Marvin M. Lateef
Assistant Examiner—Ali M. Imam
(74) Attorney, Agent, or Firm—W. Brinton Yorks, Jr.

(57) ABSTRACT

An ultrasonic diagnostic imaging system and method are described for more uniformly sector scanning a volumetric or planar image region. The acquired data set comprises raylines extending over the full depth of field and raylines for which near-field image data is omitted. This results in a more uniform spatial sampling of both the near- and far-field regions when scanning with radially steered beams. Processing and storage requirements of the ultrasound system are correspondingly lessened.

20 Claims, 4 Drawing Sheets

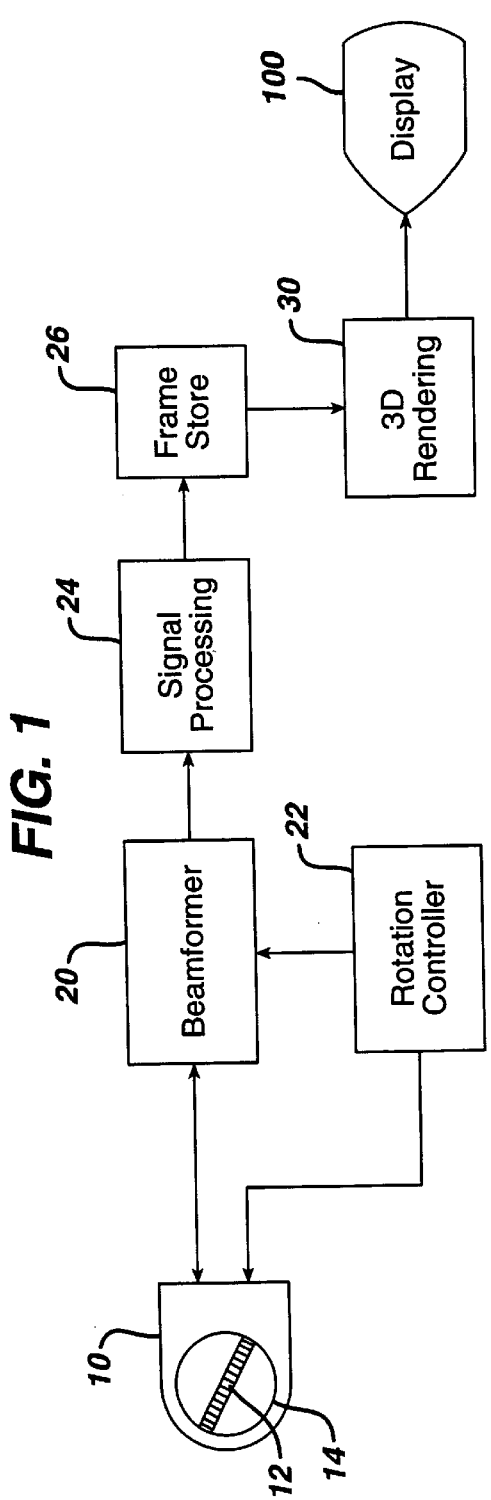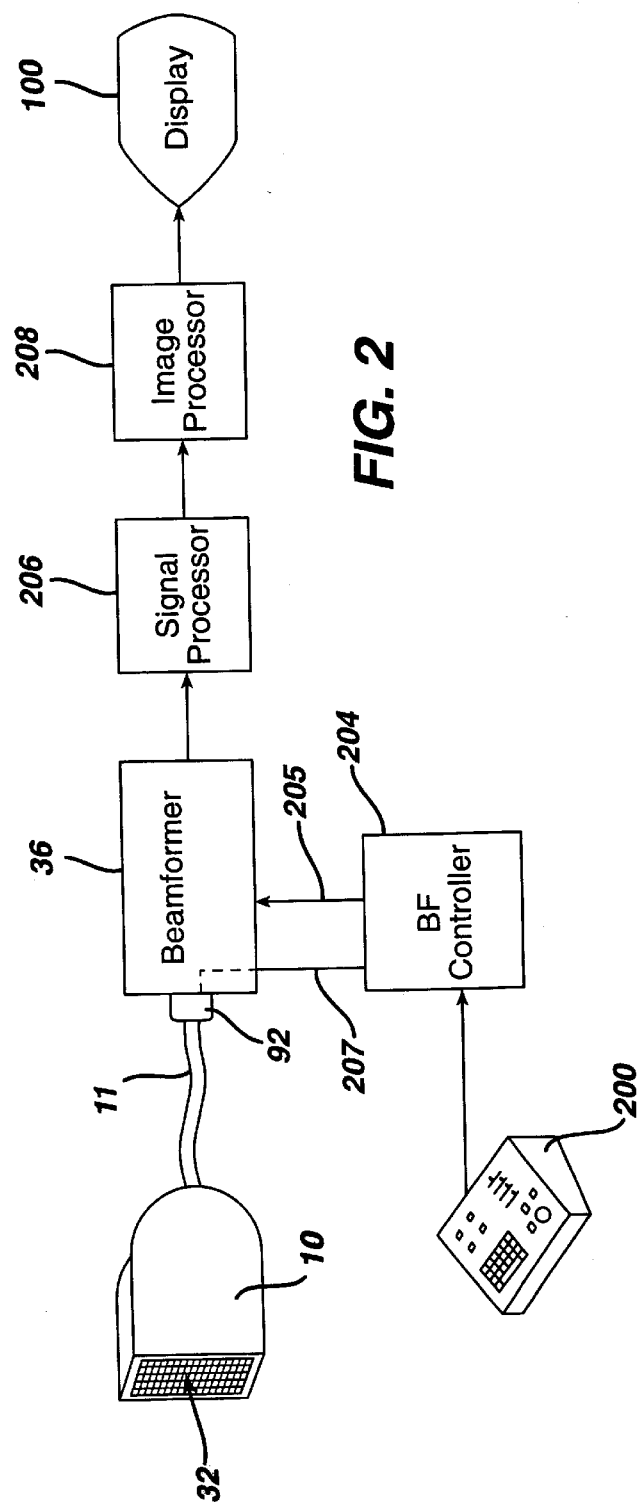

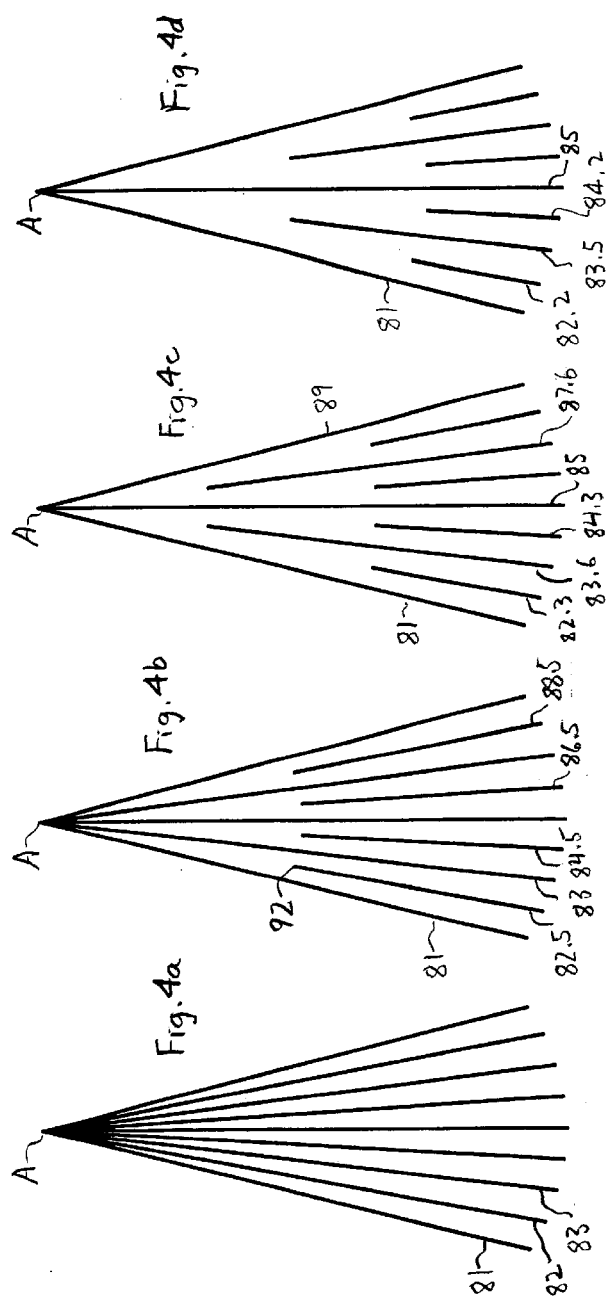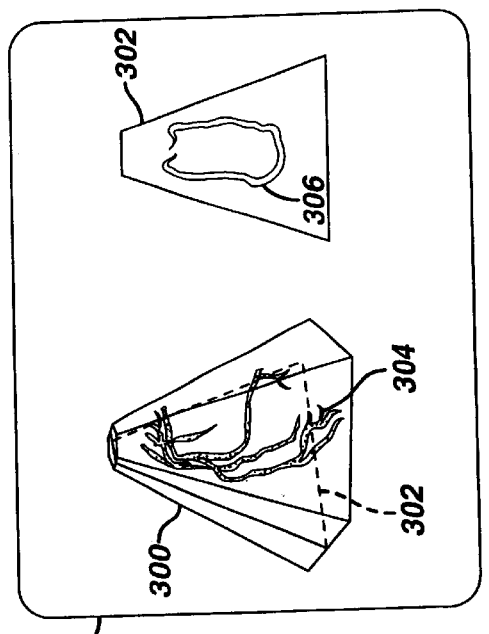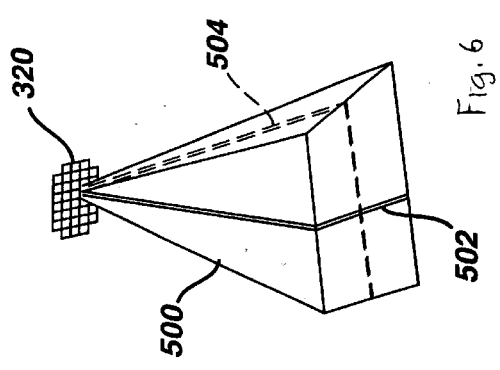

PARTIAL RAYLINE VOLUMETRIC SCANNING ULTRASONIC DIAGNOSTIC IMAGING SYSTEM

This invention relates to ultrasonic diagnostic imaging systems and, in particular, to ultrasonic diagnostic imaging systems which efficiently scan a volumetric region for three dimensional imaging.

When a volumetric region or three dimensional object is ultrasonically scanned for three dimensional imaging, it is desirable to completely and adequately sample or scan the region or object so that the resultant three dimensional image faithfully and completely represents the internal detail of the volumetric or three dimensional object. A number of techniques have been proposed for ultrasonically scanning volumetric regions with the array transducer scanheads widely in use today for conventional two dimensional planar imaging. One of these techniques is to rotate the scanhead about a pivot point. This technique will sweep the image plane through a cylindrical or conical volume of the body when the scanhead is rotated about the center of the image plane, depending upon whether the scan plane is linear or sector shaped. Both external and internally operating scanheads have been developed for performing this scanning. The article "Multidimensional Ultrasonic Imaging for Cardiology" by McCann et al., published in the *Proceedings of the IEEE*, vol. 76, no. 9 (September 1988) at pages 1063–73 illustrates the rotational scan plane technique and describes an externally applied scanhead which scans the heart transthoracically. The scan plane is rotated by rotating a phased array transducer in angular increments with a stepper motor. The use of the motor enables uniform control of the angular rotational increments; in an illustrated application the scan plane is stepped in increments of exactly 1.8°. The rotational volumetric scanning technique can also be performed internal to the body with a multiplane transesophageal echocardiography (TEE) probe as described in U.S. Pat. No. 5,181,514. Since a multiplane TEE probe inherently performs the function of rotating an array transducer about its center, successive scan planes can be acquired and stored as the array transducer is rotated and then used to form a three dimensional image.

Another technique for radially scanning a volumetric region is with a two dimensional array transducer which electronically steers beams in different radial directions. With elements extending in two dimensions, the beams transmitted and received by a two dimensional array can be steered to electronically scan a conical or pyramidal volume by phased timing of the array elements. The use of a two dimensional array to scan a volumetric pyramid is shown in the article "A Two-Dimensional Array for B-mode and Volumetric Imaging with Multiplexed Electrostrictive Elements, by R. E. Davidsen et al., *Ultrasonic Imaging*, vol 19 at pp 235–250 (1997). A complete ultrasound system for electronically scanning a volume with radially steered beams is shown in U.S. patent application Ser. No. 09/919,681, entitled "Three Dimensional Ultrasonic Diagnostic Imaging With High Density Hexagonal Acquisition" by Cooley et al.

An improved rotational scanning technique for a volumetric region is described in U.S. patent application Ser. No. 09/433,124 by Lennon. Lennon has taken cognizance of the fact that the scanned beams are more closely spaced at the center of the volumetric region, and more widely spaced at the lateral periphery of the region. Lennon describes how to more uniformly spatially sample the volume by spreading the beams in the center of the volume and more closely spacing the beams at the periphery. This technique reduces the oversampling of the volumetric region at the center and the undersampling of the region at its periphery as the scanning plane is rotated through the volume.

The Lennon technique, while dealing with lateral spatial sampling variation, does not address another problem encountered in radial volumetric scanning, which is the axial spatial sampling variation. In the axial or depth dimension, conventional radial scanning results in a greater sampling density at and near the apex of the volume next to the transducer than is the case at deeper depths of the volume. This is true in both mechanical scanning with a one dimensional array and electronic scanning with a two dimensional array. It is desirable to be able to reduce or eliminate this axial sampling disparity in radial volumetric scanning. It is further desirable to improve the efficiency of the imaging system when doing so.

In accordance with the principles of the present invention, a technique and apparatus are provided for overcoming the disparity in sampling density between the near field and the far field when radially scanning a planar or volumetric region. This is accomplished by processing only partial raylines which have near field portions eliminated. The near field portions of some of the raylines can be discarded, thereby conserving image storage space and easing image processing demands. Alternatively, the partial raylines are only acquired in the far field. The partial raylines can also be formed by multiline acquisition or lateral interpolation which operates in the far field.

In the drawings:

FIG. 1 illustrates in block diagram form an ultrasonic volumetric imaging system and 1D array probe constructed in accordance with the principles of the present invention;

FIG. 2 illustrates in block diagram form an ultrasonic volumetric imaging system and 2D array probe constructed in accordance with the principles of the present invention;

FIGS. 4a–4d illustrate three examples of partial rayline scanning techniques in accordance with the principles of the present invention;

FIG. 6 illustrates the scanning of a three dimensional volume and two planar regions within that volume; and FIG. 7 illustrates a duplex display of the three dimensional volume and a two dimensional image plane of FIG. 6.

Figure 3:
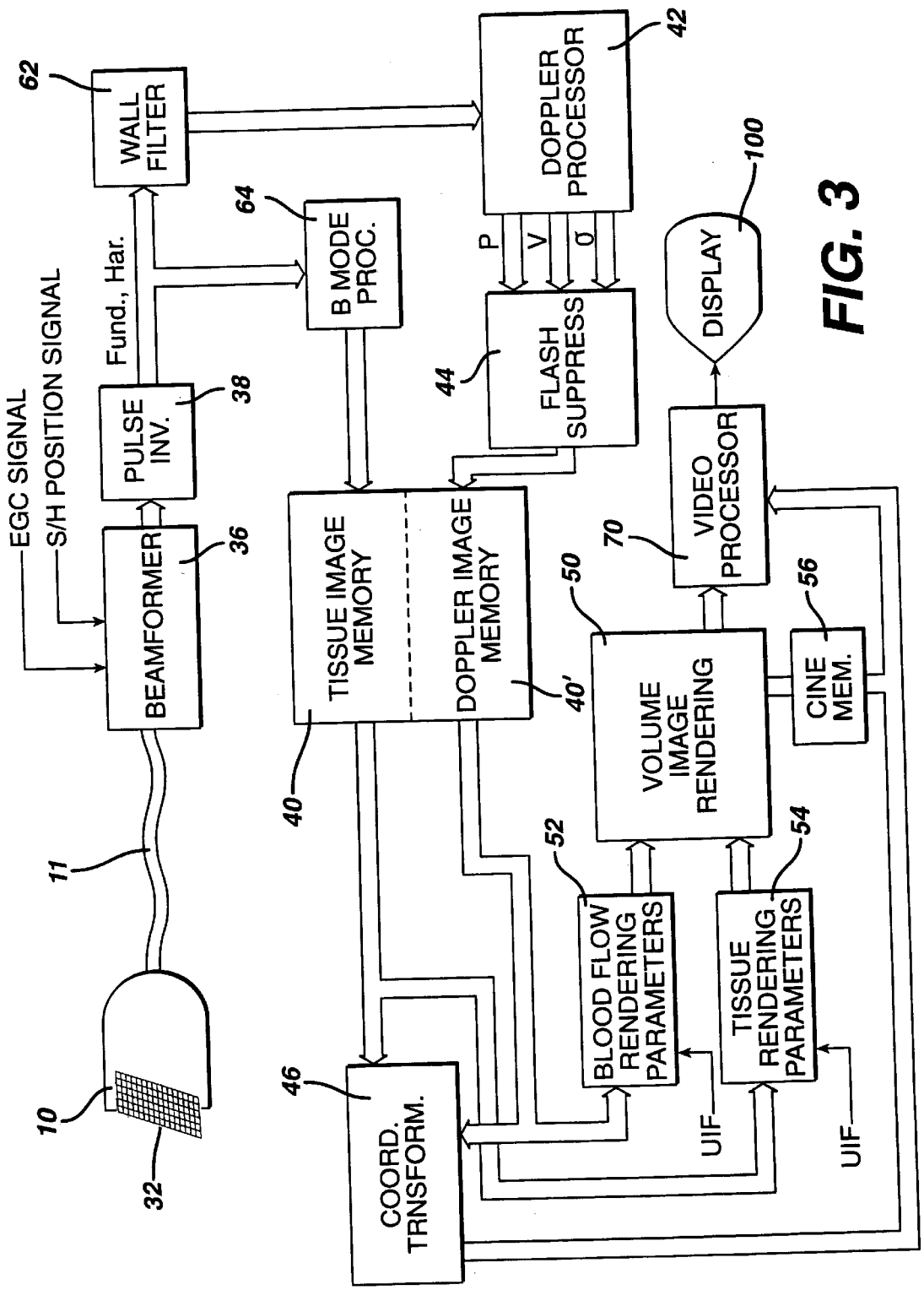
FIG. 3 illustrates in block diagram form the processing of volumetric data in a 3D ultrasonic imaging system.

Referring first to FIG. 1, an ultrasonic diagnostic imaging system and scanhead constructed in accordance with the principles of the present invention are shown. The scanhead 10 includes a housing in which a rotating transducer array 12 is located. The transducer array 12 is rotated in a circular aperture 14. The illustrated array 12 is a one dimensional (1D) array which steers beams in the azimuth direction of a scan plane. Such a transducer array is mechanically rotated by a motor in the housing, under control of a rotation controller 22. The motor may be a linear or stepper motor of a multiplane TEE probe as described in U.S. Pat. No. 5,402,793 and 5,181,514, or the motor of a trans-thoracic rotating array probe such as that described by McCann et al. and in U.S. Pat. No. 5,779,639. As the motor rotates the array transducer, its scan plane is rotated about the axis of rotation. Preferably the axis of rotation passes through the center of the array, that is, the array transducer is rotated about its center, but embodiments in which the array transducer is rotated about an off-center axis are also possible.

The scanhead 10 is coupled to a beamformer 20 which controls the transmit steering and focusing of the beams produced by the array transducer 12, and the steering and dynamic focusing of received beams. In a preferred embodiment the beamformer is a multiline beamformer which is capable of producing multiple, spatially discrete beams in response to a single transmit event. The scanhead 10 is also coupled to the rotation controller 22 as described above. When the rotation controller 22 performs mechanical rotation of the array transducer, rotational information is provided to the beamformer 20 so that the transmission and reception of beams is coordinated with the position of the transducer. The rotational information may be provided by a shaft encoder or counter, for example, which tracks rotation of the transducer array. In this manner, the beamformer controls the array transducer to scan a volumetric region of the body with ultrasonic beams.

The coherent receive beams formed by the beamformer 20 are coupled to signal processing circuitry 24. The signal processing circuitry operates as is known in the art to produce ultrasonic image signals of tissue, motion or flow. In a preferred embodiment the signal processing circuitry also performs lateral interpolation, which produces interpolated rayline data values between received raylines. The signal processing circuitry can process fundamental or harmonic signals for detection and processing as grayscale or Doppler image signals, for instance. Filtering and compounding of the ultrasound signals may also be performed by the signal processing circuitry. The image signals are then stored in a frame store 26 in correspondence to their locations in a volumetric data array or a series of planar data arrays. The frame store may also include scan conversion functions to further process or orient the image signals into a desired display format with polar or rectilinear coordinates.

The image signals acquired from a volumetric region of the body are coupled to a 3D rendering processor 30. The 3D rendering processor may use any type of known processing to form a 3D image presentation. The 3D rendering processor may process the volumetric data to form a surface rendering, which is useful for 3D imaging of the face of a fetus or the wall or surface of an organ such as the heart. The 3D rendering processor may also perform volume rendering, which is useful to form a 3D image of vascular flow such as the coronary or renal arteries, as described in U.S. Pat. No. Re36,564. In any case, the 3D display signals produced by the 3D rendering processor are coupled to a display device 40 which is capable of displaying the desired three dimensional ultrasonic image.

FIG. 2 illustrates a 3D imaging ultrasound system with a two dimensional (2D) array transducer 32. When the array transducer is a 2D array, beams can be electronically steered in both azimuth and elevation. In such case it is not necessary to mechanically rotate the transducer. The beams can be steered electronically in both elevation and azimuth about a central axis of the volumetric region by control of the steering delays of transmit and receive beamforming. The transducer probe 10 in this embodiment includes a 2D array 32. The transducer probe is connected to the ultrasound system beamformer 36 by a cable 11 and a probe connector 92. The beamformer 36 controls the times at which signals are applied to the elements of the 2D array which are used for transmission, and delays and combines signals received from the elements for the transmission of steered and focused beams and for the dynamic focusing and steering of received echo signals over a planar or volumetric region. As in the first embodiment, a multiline beamformer is preferred for 3D imaging. Operation of the beamformer is controlled by a beamformer controller 204 which controls the timing, steering, frequency, and focusing of transmitted and received beams in the normal manner by data coupled to the beamformer 36 over a data bus 205. In addition, the beamformer controller 204 provides data over MUX control lines 207 which controls the setting of the switches that connect selected elements of the 2D array to each other for aperture control and to the beamformer 36 over the cable 11. The beamformer controller 204 controls the beamformer in response to inputs from the user by way of the user interface 200, which may comprise a control panel or softkeys on the system display screen. For example, the user may command the system to acquire a three dimensional harmonic image and also to periodically acquire a two dimensional Doppler flow image within the three dimensional volume. The beamformer controller would then control the probe and beamformer to switch back and forth between these different modes in a time interleaved manner. The beamformed signals are used for interpolation as desired and are B mode or Doppler processed by a signal processor 206 and formed into an image of the desired format and orientation by an image processor 208 for display on an image display 100.

FIG. 3 shows another embodiment of the present invention which illustrates three dimensional image processing in further detail. A probe 10 including an array transducer 32 is connected by a cable 11 to a beamformer 36. The beamformer controls the timing of actuation signals applied to the elements of the transducer array for the transmission of steered and focused transmit beams, and appropriately delays and combines signals received from the transducer elements to form coherent echo signals along the raylines delineated by the transmit beams. The timing of the beamformer transmission is also responsive to an ECG signal when it is desired to synchronize or gate image acquisition with a particular phase of the heart cycle.

The output of the beamformer, which again is preferably a multiline beamformer, is coupled to a pulse inversion processor 38 for the separation of fundamental and harmonic frequency signals. Pulse inversion processors are well known in the art and are described in U.S. Pat. Nos. 5,706,819 and 5,951,478. These patents describe how echoes from alternately phased pulses can be used to separate harmonic tissue or contrast signals from fundamental frequency signals.

The fundamental and/or harmonic signals may be B mode processed or Doppler processed, depending upon the desired information to be displayed. For Doppler processing the signals are coupled to a wall filter 62 which can distinguish between flow, stationary tissue, and moving tissue. A preferred wall filter for contrast imaging is described in U.S. Pat. application Ser. No. 09/156,097, which is also capable of performing harmonic contrast signal separation. The filtered signals are applied to a Doppler processor 42, which produces Doppler power, velocity, or variance estimation. A preferred Doppler processor for harmonic Doppler signal estimation is described in U.S. Pat. No. 6,036,643. Artifacts from scanhead motion which can contaminate Doppler imaging are removed by a flash suppressor 44. Various techniques may be used to remove flash artifacts prior to or subsequent to image formation, including the notch filter technique described in U.S. Pat. No. 5,197,477 and the min-max filter technique described in U.S. Pat. No. 5,782,769. The processed Doppler signals are stored in a Doppler image memory 40'.

Signals which are to be B mode processed are applied to a B mode processor 64 which detects the signal amplitude. B mode processed signals are stored in a tissue image memory 40.

The B mode and Doppler signals are applied to a coordinate transformation processor 46. For conventional two dimensional imaging the coordinate transformation processor will function as a scan converter, remapping polar coordinate data to Cartesian coordinates as necessary and filling spaces between received lines with interpolated image data. The scan converted images are coupled to a video processor 70 which puts the image information into a video format for display of the images on a display 100. The images are also coupled to a Cineloop® memory 56 for storage of a loop or sequence of images when that function is invoked by the user.

When 3D imaging is being performed by the ultrasound system, the coordinate transformation processor may be used to scan convert the tissue and Doppler signals in planes of image information over the scanned volume, or may be used to transform the coordinates of the image data into a three dimensional data matrix. Scan conversion also usually involves the interpolation of display data points which are uniform over the volume being displayed. Preferably the coordinate transformation processor operates in cooperation with a volume rendering processor 50, which can render a three dimensional presentation of the image data which has been processed by the coordinate transformation processor. Three dimensional images of tissue are rendered in accordance with tissue rendering parameters 54 which are selected by the user through a control panel or user interface (UIF). Three dimensional images of Doppler information are rendered in accordance with blood flow rendering parameters 52. These parameters control aspects of the rendering process such as the degree of transparency of tissue in the three dimensional image, so that the viewer can see the vasculature inside the tissue. This capability is important when 3D images of both tissue and flow are being rendered, as described in U.S. Pat. No. 5,720,291. Three dimensional images can be stored in the Cineloop® memory 56 and replayed to display the scanned volume in a dynamic parallax presentation, for instance. A three dimensional rendering of flow without the surrounding tissue, as described in U.S. Pat. No. Re 36,564, can reveal the continuity of flow of blood vessels and obstructions in those vessels and is useful for applications such as evaluating the vasculature of a transplanted organ.

In accordance with the principles of the present invention, imaging is performed by the use of partial raylines. In this approach, only the lower (deeper) portions of selected raylines are processed, as illustrated in FIGS. 4a–4d. FIG. 4a illustrates the acquisition of a conventional radial pattern for a sector image. The raylines are acquired by transmitting a beam along each rayline 81, 82, 83, etc. and receiving a sequence of echoes from along the rayline following each transmission. For higher speed acquisition multiline reception may be employed, whereby two or more raylines are insonified at the same time and echoes received along multiple raylines simultaneously. Received raylines are formed simultaneously by using two or more sets of delays to steer and focus two or more raylines at the same time. The transducer array is located at the top of the sector. The apex A of the sector may be located at the transmitting surface of the array, or behind the transmitting surface for a virtual apex sector as described in U.S. Pat. No. 5,123,415 or for a curved linear array.

FIG. 4b illustrates an embodiment of the present invention in which alternate raylines are partial raylines. This is referred to as a {1-½-1} rayline pattern, where the 1's indicate full raylines such as raylines 81 and 83 in FIG. 4b and "½" indicates a partial rayline which extends over the deeper half of the sector, as shown by rayline 82.5. During acquisition the beamformer can ignore rayline 82.5 until echoes are received from the shallowest depth 92 of the partial rayline and only acquire rayline 82.5 thereafter. Alternately, a full rayline can be acquired and the shallow depth half discarded at some point in the signal processing path so that only the deeper half of the rayline is used in image processing. To increase the frame rate the partial raylines 82.5, 84.5, 86.5, 88.5 are produced by either multiline acquisition or r.f. interpolation. For instance, raylines 82.5, 83 and 84.5 can be insonified by a single transmit event, with partial raylines 82.5 and 84.5 received simultaneously in multiline acquisition during the latter half of the period of reception of full rayline 83. R.f. interpolation can also be employed to form the partial raylines by laterally interpolating the received data from the deeper portions of raylines 81 and 83 to form partial rayline 82.5 by computing (½R81+½R83) at each incremental depth where a value for rayline 82.5 is desired. In a preferred embodiment the received rayline data is used to interpolate both partial and full raylines for the image field in order to eliminate the motion artifact which arises from a mixed sequence of image lines from different apertures, as described in U.S. Pat. No. 6,228,031. In either case, the number of transmit events required to acquire the sector data is reduced by the use of multiline reception or r.f. interpolation, thereby decreasing the time required to form the raylines for the sector and increasing the frame rate of display.

FIG. 4c illustrates another embodiment of the present invention which uses a {1-⅓-⅔-⅓-1} rayline pattern. It is seen that rayline 81 is a full rayline, rayline 82.3 extends over only the lower one-third of the sector depth, rayline 83.6 extends over the lower two-thirds of the sector depth, rayline 84.3 extends over the lower one-third of the sector depth, and rayline 85 is a full rayline. The sequence then repeats with rayline 85 counted as the first rayline of the next sequence. As in the previous embodiment, the partial raylines can be formed in response to discrete transmit beams, or by multiline reception or by r.f. interpolation. The partial raylines may also be formed by a combination of both techniques. For instance, a single transmit event could insonify raylines 81, 83.6, and 85, with all three being formed simultaneously by multiline beamforming. Lateral r.f. interpolation can then be used to form partial rayline 82.3 by interpolating between rayline 81 and partial rayline 83.6, and partial rayline 84.3 can be formed by interpolating between partial rayline 83.6 and rayline 85, in each case over the lower one-third of the sector depth. As mentioned above, it is preferable to form all of the raylines for the image by interpolation of the received data in order to reduce the susceptibility to motion artifacts due to the varying apertures. This combination of multiline reception and r.f. interpolation can result in a four-fold reduction in acquisition time and a corresponding improvement in frame rate.

FIG. 4d illustrates another embodiment of the present invention which uses a {1-¼-½-¼-1} rayline pattern. It is seen in this embodiment that rayline 81 is a full rayline, rayline 82.2 extends over only the lower one-quarter of the sector depth, rayline 83.5 extends over the lower one-half of the sector depth, rayline 84.2 extends over the lower one-quarter of the sector depth, and rayline 85 is a full rayline. The sequence then repeats. As in the previous embodiment, acquisition can be performed by multiline reception, r.f. interpolation, or a combination of the two in the same manner as in the embodiment of FIG. 4c.

While FIGS. 4b–4d illustrate three possible patterns of full and partial raylines, other patterns will readily occur to those skilled in the art.

A benefit of the partial rayline technique is that an image with substantially equivalent near-field and far-field lateral resolution can be processed and displayed with less data storage and processing power. Mid- and near-field image quality is not noticeably degraded by the absence of the partial rayline information, as there is still sufficient line density (spatial sampling) in these regions for most scan conversion and volume rendering algorithms to operate successfully. The previous examples of a {1-½-1} rayline pattern shown above reduces storage and processing requirements by 25%, the {1-⅓-⅔-⅓-1} rayline pattern reduces storage and processing requirements by 33%, and the {1-¼-½-¼-1} rayline pattern reduces storage and processing requirements by 50%. These reductions enable an ultrasound system to be produced with less signal processing power and data storage capability than a conventional system or, conversely, enable a system to achieve higher levels of lateral interpolation with the same processing power as conventional acquisition.

In applications where the order of lateral interpolation is limited by the ultrasound system's processing capability rather than image quality requirements, the inventive technique allows higher frame rates to be achieved. For example, a conventional system with two parallel processing paths can process acquired echo data using 2× multiline or 2× r.f. interpolation, but not both. The partial rayline technique of the present invention allows both 2× multiline and 2× r.f. interpolation to be used, as demonstrated above, thereby generating four raylines per transmit event. The whole and partial raylines can be processed with no increase in overall processing power as 1 full rayline, 1 half rayline, and 2 quarter raylines following one transmit event, resulting in a 100% improvement in frame rate for the same line density.

Even when frame rate is not limited by processing capability, the partial rayline technique can provide frame rate improvement during multizone imaging, where a full rayline is acquired in discrete depth segments, enabling the transmit beam to be focused in a particular depth zone during each acquisition. For example, the {1-⅓-⅔-⅓-1} pattern of FIG. 4c can be particularly useful for three, single focal point focal zones when the zone transitions are aligned with the shallowest points of each new set of partial raylines. During acquisition of the shallowest zone, only raylines 81, 85, and 89 would be transmitted and received. During acquisition of the mid-field zone, only raylines 81, 83.6, 85, 87.6, and 89 would be transmitted and received. During acquisition of the far-field zone, all raylines would be transmitted and received. This results in an improvement in frame rate compared to the conventional multizone approach of transmitting every line in every zone.

Figure 5:
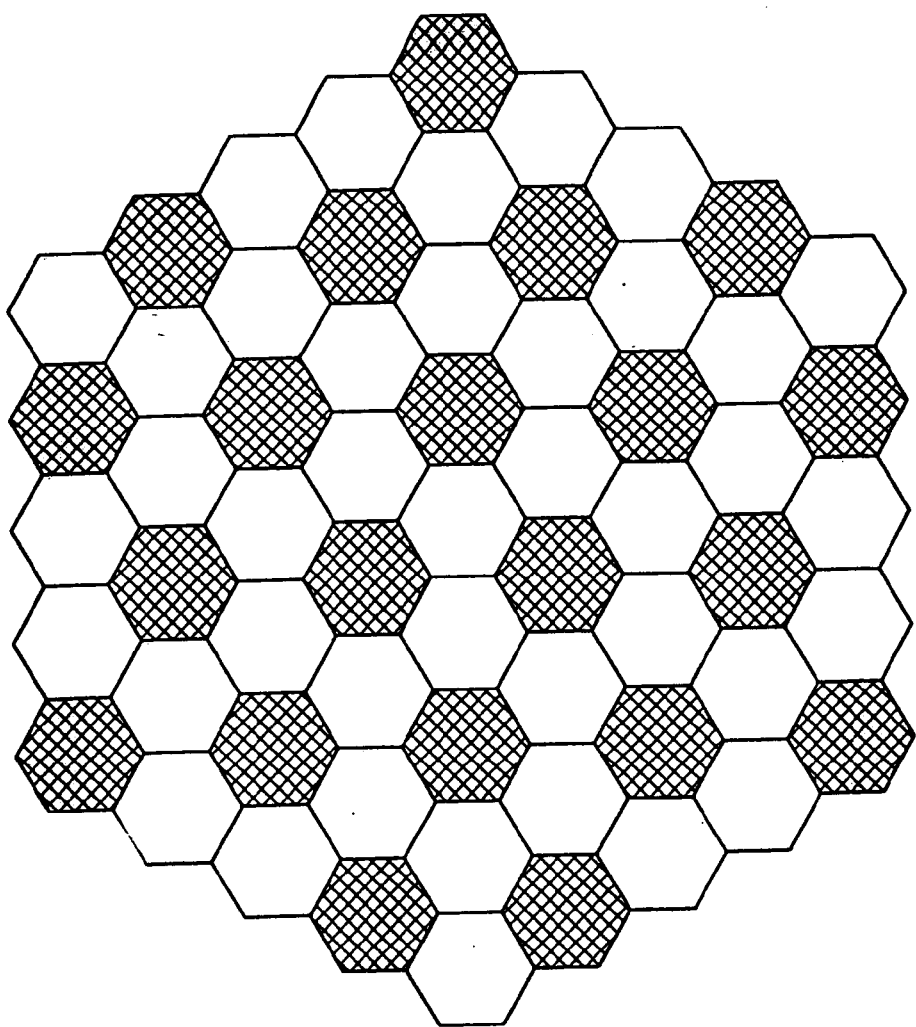
FIG. 5 illustrates an example of the rayline spacing in a lateral plane through a volumetric region scanned in accordance with the present invention.

The partial rayline embodiments of FIGS. 4b–4d illustrate the raylines of a single plane such as would be scanned by a linear array transducer 12 of FIG. 1. Such a plane of whole and partial raylines is acquired at each angular increment of rotation of the transducer array until a full volume has been scanned. An individual plane of the volume may then be processed for display, or the 3D data set of the scanned volume may be volume rendered for a three dimensional image display. When a 2D array such as array 32 is used to electronically scan a three dimensional volume, the raylines may be acquired in any desired spatial sequence, planar or non-planar. A lateral slice through the spatially-oriented raylines where partial rayline data is absent would show the absence of these raylines, as illustrated in the planar cut of FIG. 5 through the mid- or near-field region of the volume. In this drawing the cross-hatched hexagons are locations where a full rayline has been acquired, and the clear hexagons are locations where only partial raylines are present at deeper depths in the volume. This data set has been acquired by hexagonal scanning, as described in U.S. patent application Ser. No. 09/912,785 entitled "Ultrasonic Diagnostic Imaging System with Hexagonal Scanning," and is but one example of a pattern of mixed full and partial raylines in three dimensional scanning.

Another application where the partial rayline technique is of significant benefit is when r.f. image data is being saved for later image processing. For example, a sequence of images can be stored in a Cineloop® memory 56 as shown in FIG. 3. Instead of capturing and storing the display image data, the r.f. data for the images can be saved. This enables the sequence to be replayed with different image processing, which may reveal different diagnostic features in the region being imaged. Since an r.f. data set, particularly from all of the elements of an array transducer, is much more sizeable than a display (detected) data set, a given size of Cineloop memory will hold far fewer r.f. images than display images. The number of r.f. images is increased when partial rayline data sets are used, since the size of a partial rayline data set is less than a full rayline data set of the same far-field rayline density. Even more image can be stored in a given buffer if interpolated raylines are not produced until the stored r.f. data is recalled for processing and display.

FIG. 6 illustrates the acquisition of planar image data in a volumetric region. In this drawing a 2D array 320 is operated to scan two planar images within a volumetric region 500. The array 320 is operated as an electronically steered 2D array which scans a pyramidal volumetric region 500 with radially steered raylines. Instead of scanning the entire pyramidal volume, the array can scan either two dimensional plane 502 or two dimensional plane 504, or both, using partial rayline acquisition. A desirable format for this mode of imaging would be to display a three dimensional image of the volumetric region 500 with an adjacent planar image of one or both of planes 502 and 504 as shown in FIG. 7 by three dimensional image 300 and planar image 302 taken through cut plane 302 in the volumetric image 300. As the probe is moved in relation to the body, anatomy such as blood vessels 304 would move into and out of the volumetric region 300 (500), and more quickly into and out of the image plane 302 (502 or 504) as illustrated by anatomical portion 306. The clinician can thus scan the body in three dimensions and in one or two image planes in real time. When arrays having a grid pattern other than a rectilinear one are employed, such as the hexagonal 2D array described in U.S. patent application Ser. No. 09/488,583 filed Jan. 21, 2000, the image planes may be oriented on planes aligned with the grid pattern. A hexagonal 2D array may produce two or three image planes separated by 60 degrees rather than two image planes separated by 90 degrees, for instance.

What is claimed is:

1. A method for reducing storage or processing requirements in ultrasonic imaging by sector scanning a region of interest comprising:

scanning the region of interest with radially steered beams;

acquiring rayline data from along at least a portion of the radially steered beams;

image processing the rayline data in which the data for the near-field portion of some of the raylines has been omitted; and storing or displaying the processed rayline data.

2. The method of claim 1, wherein image processing further comprises image processing the rayline data in which the data for the near-field portion of some of the raylines has been omitted to more closely equalize near-and far-field spatial sampling.

3. The method of claim 1, wherein acquiring comprises acquiring rayline data from both the near-and far-field for some raylines and acquiring rayline data from only the far-field for other raylines.

4. The method of claim 1, wherein acquiring comprises acquiring rayline data from both the near-and far-field for a group of raylines; and further comprising omitting the near-field portion of some of the raylines during signal processing.

5. The method of claim 1, wherein acquiring comprises acquiring rayline data from both the near-and far-field for a group of raylines; and further comprising omitting the near-field portion of some of the raylines during signal processing.

6. The method of claims 1, wherein acquiring comprises acquiring rayline data from along the full depth of field of the radially steered beams.

7. The method of claim 1, wherein storing or displaying comprises displaying a planar image.

8. The method of claim 1, wherein storing or displaying comprises displaying a three-dimensional image.

9. The method of claim 1, wherein image processing comprises image processing a spatial sequence of raylines of the form of $\{1\text{-}\frac{1}{2}\text{-}1\}$ wherein 1 represents a full-depth rayline and the fraction represents the partial rayline portion remaining after omission of a near-field portion.

10. The method of claim 1, wherein image processing comprises image processing a spatial sequence of raylines of the form of $\{1\text{-}\frac{1}{3}\text{-}\frac{2}{3}\text{-}\frac{1}{3}\text{-}1\}$ wherein 1 represents a full-depth rayline and the fraction represents the partial rayline portion remaining after omission of a near-field portion.

11. The method of claim 1, wherein image processing comprises image processing a spatial sequence of raylines of the form of $\{1\text{-}\frac{1}{4}\text{-}\frac{1}{2}\text{-}\frac{1}{4}\text{-}1\}$ wherein 1 represents a full-depth rayline and the fraction represents the partial rayline portion remaining after omission of a near-field portion.

12. A method of partial rayline imaging of a region of the body scanned by radially directed raylines comprising:

acquiring full image data from both the near-field and far-field regions of a plurality of radially directed, spatially distinct raylines; and acquiring first partial image data from only the far-field regions of a plurality of radially directed, spatially distinct raylines which are interspaced between the raylines for which both near-field and far-field data was acquired; and forming an image using the full and first partial image data.

13. The method of claim 12, wherein forming an image comprises forming a planar image.

14. The method of claim 12, wherein forming an image comprises forming a three-dimensional image.

15. The method of claim 12, wherein forming an image comprises scan converting the acquired image data.

16. The method of claim 12, wherein acquiring first partial image data comprises receiving partial raylines by multiline acquisition.

17. The method of claim 12, wherein acquiring first partial image data comprises producing partial image data by lateral r.f. interpolation of spatially adjacent image data.

18. The method of claim 12, further comprising acquiring second partial image data from only the more distant far-field regions of a plurality of radially directed, spatially distinct raylines than the far-field regions of the first partial image data raylines, which second partial image data raylines are interspaced between the full and first partial raylines; and forming an image using the full and first and second partial image data.

19. A method for acquiring multi-zone focused ultrasonic image data comprising:

transmitting a first plurality of radially steered rayline segments over a near-field zone of an image field and receiving echo data from along the rayline segments;

transmitting a second plurality of radially steered rayline segments over a far-field zone of an image field and receiving echo data from along the rayline segments, wherein the second plurality of rayline segments is at greater than the first plurality; and forming an image from the rayline segments of the first and second plurality.

20. The method of claim 19, wherein transmitting the second plurality of rayline segments further comprises forming at least some of the rayline segments by r.f. interpolation.

* * * * *